US00PP09010P

United States Patent [19]

Austin

[11] Patent Number: Plant 9,010

[45] Date of Patent: Dec. 13, 1994

[54] SHRUB ROSE PLANT NAMED AUSWITH

[75] Inventor: David C. H. Austin, Albrighton, England

[73] Assignee: David Austin Roses Limited, Albrighton, England

[21] Appl. No.: 183,276

[22] Filed: Jan. 13, 1994

[51] Int. Cl.[5] ..... A01H 5/00

[52] U.S. Cl. ..... Plt./1

[58] Field of Search ..... Plt. 1, 22

U.S. PATENT DOCUMENTS

PLT 8679 Austin ..... PLT/1

PLT 8680 Austin ..... PLT/1

*Primary Examiner*—Howard J. Locker

*Attorney, Agent, or Firm*—Klarquist Sparkman Campbell Leigh & Whinston

[57] ABSTRACT

A shrub rose having large, fully double rosette flowers that are repeat flowering, generally pale pink in color, the color of the petals varying on each flower.

1 Drawing Sheet

The present invention relates to a new and distinct variety of rose plant of the shrub class which was originated by me by crossing the variety AUSmary with an unnamed seedling.

The primary objective of this breeding was to produce a new shrub rose variety that is repeat flowering and has pink, old-fashioned-shaped flowers. The objective was substantially achieved, along with other desirable improvements, as evidenced by the following unique combination of characteristics that are outstanding in the new variety and that distinguish it from its parents, as well as from all other varieties of which I am aware:

1. Paler pink flowers than either parent;
2. Fully double rosette flowers;
3. Large blooms; and
4. Petals varying in color on each flower.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—AUSmary (unpatented).

*Pollen parent.*—Unnamed seedling (unpatented).

Classification:

*Botanical.*—*Rosa hybrida.*

*Commercial.*—Shrub.

FLOWER

Observations made from specimens grown in a garden environment at Albrighton, Wolverhampton, England.

Blooming habit: Recurrent.

Bud:

*Size.*—2 to 5 cm long when the petals start to unfurl.

*Form.*—The bud form is blunt topped, globular.

*Color.*—When sepals first divide, bud color is Red Group 37A/B. When half blown, the upper sides of the petals are Orange Group 29D; and the lower sides of the petals are Red Group 39C/D.

*Sepals.*—Color: Yellow-Green Group 144A/B. Surface texture: Fairly smooth. There are three lightly appendaged sepals. There are two unappendaged sepals with smooth, downy edges.

*Receptacle.*—Color: Yellow-Green Group 144A/B. Shape: Slender goblet. Size: About 11 mm×10 mm. Surface: Smooth.

*Peduncle.*—Length: Averaging about 2.5 to 3 cm. Surface: Glandular. Color: Medium green. Strength: Bending, heavy.

Bloom:

*Size.*—Average open size is 7 to 8 cm.

*Borne.*—Singly or several together in clusters of irregular shape.

*Stems.*—Average length is about 60 to 70 cm; normal strength.

*Form.*—When first open: Bloom is cupped, tea-rose type. Permanence: Flattens to form a rosette with a quartered or button center. Outer petals curl back. Outer petal edges curl slightly.

*Petalage.*—Number of petals under normal conditions: 120 to 130.

*Color.*—The upper side of the petals is: Outer petals: Orange Group 27C/D. Inner petals: Red Group 36A/C. The reverse side of the petals is: Outer petals: Orange Group 27D. Inner petals: Red Group 36C. The base of each petal has a yellow tinge, Yellow Group 12C, deepening to Yellow Group 12A at the tip. The major color on the upper side is Red Group 36A/C.

*Variegations.*—None.

*Discoloration.*—The general tonality at the end of the first day: Paler, less orange, more pink/yellow than at beginning of first day. At the end of the third day, Red Group 36D, much paler than on first day.

*Fragrance.*—Moderate citrus/musk.

Petals:

*Texture.*—Soft.

*Shape.*—Outer: round, notched. Inner: more ovoid, deltoid, with a flat top.

*Form.*—Tips slightly curved; outer petals' edges slightly quilled.

*Arrangement.*—Quartered rosette, with central petals tucked into calyx, and few petaloids in the center.

*Persistence.*—Petals drop off cleanly before drying.

*Lastingness.*—On the plant: 3 to 4 days. As a cut flower: 3 to 4 days.

Reproductive parts:

*Anthers.*—Size: Medium. Quantity: Many. Color: Golden yellow. Arrangement: Regular around styles; mixed with petaloids.

*Filaments.*—Color: Yellow.

*Pollen.*—Color: Gold yellow.

*Styles.*—Color: Yellow-Green Group 149D (but paler).

*Stigmas.*—Color: Yellow.

Form: Shrub.

Growth: Vigorous.

Foliage: Usual number of leaflets on normal mid-stem leaves: 5 (occasionally 7).

*Size.*—About 13 to 14 cm long×10 to 11 cm wide.

*Quantity.*—Normal distribution of leaves on stem for this class.

*Color.*—New foliage: Yellow-Green Group 146A/B with Greyed-Red 178A blush on margins. Old foliage: Yellow-Green Group 147A.

Leaflets:

*Shape.*—Pointed oval.

*Texture.*—Upper side: Leathery.

*Edge.*—Serrated.

*Serration.*—Small.

*Petiole rachis.*—Color: Green.

*Petiole underside.*—1 to 3 small prickles per internode, and slightly glandular.

*Stipules.*—About 2.2 cm long, with glandular edges.

*Disease resistance.*—Resistant to mildew and blackspot under normal growing conditions at Albrighton, Wolverhampton, England.

Wood:

*New wood.*—Color: Light green; slightly reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium length; hooked downward.

*Color when young.*—Red, turning transparent.

Small prickles:

Quantity.—On main stalks: Few. On laterals: Many.

*Color.*—Pinkish/transparent.

I claim:

1. A new and distinct variety of rose plant of the shrub class, substantially as herein shown and described, characterized particularly as to novelty by the unique combination of its repeat flowering, large, fully double rosette flowers that are generally pale pink in color, the color of the petals varying on each flower.

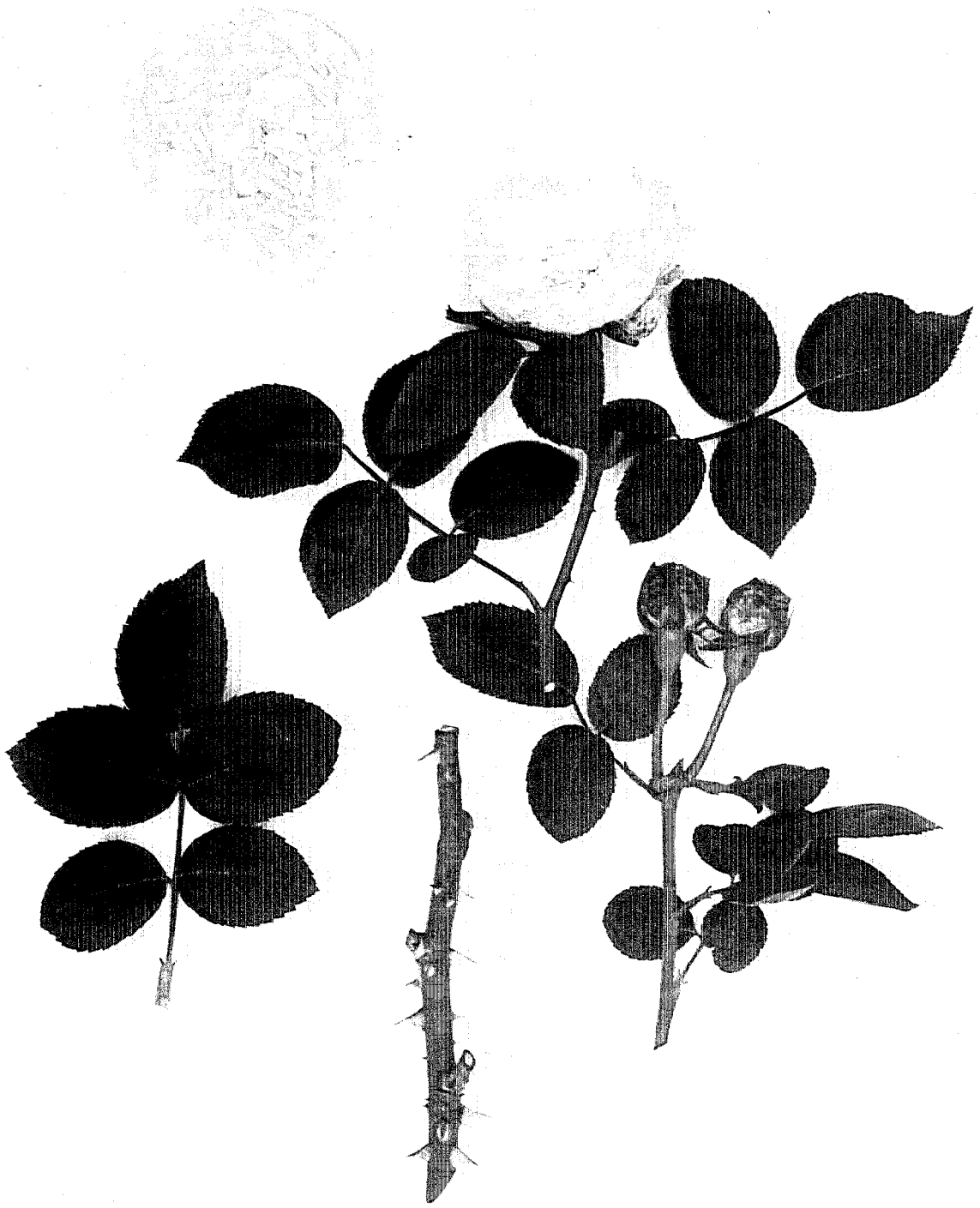

* * * * *